(12) United States Patent
Eckert et al.

(10) Patent No.: US 7,226,627 B1
(45) Date of Patent: Jun. 5, 2007

(54) GRAPESEED, COLD-PRESSED GRAPE OIL, CRUSHED GRAPE AND GRAPE FLOUR

(76) Inventors: Peter Eckert, Auf Dem Heidgen 29, Bonn (DE) D-53127; Winfrid Heinen, Tannenweg 6, Darmstadt (DE) D-54340; Carola Knaudt, Im Jagdfeld 13, Bonn (DE) D-53125

( * ) Notice: Subject to any disclaimer, the term of this patent is extended or adjusted under 35 U.S.C. 154(b) by 25 days.

(21) Appl. No.: 10/048,900

(22) PCT Filed: Aug. 2, 2000

(86) PCT No.: PCT/EP00/07460

§ 371 (c)(1),
(2), (4) Date: Nov. 7, 2002

(87) PCT Pub. No.: WO01/10987

PCT Pub. Date: Feb. 15, 2001

(30) Foreign Application Priority Data

Aug. 5, 1999 (DE) ................................ 199 36 492
Mar. 25, 2000 (DE) ................................ 100 15 006

(51) Int. Cl.
*A61K 36/78* (2006.01)
*A61K 36/00* (2006.01)

(52) U.S. Cl. ....................................... 424/766; 424/725

(58) Field of Classification Search ............. 424/195.1, 424/725, 766, 776
See application file for complete search history.

(56) References Cited

U.S. PATENT DOCUMENTS 6,544,534 B2 * 4/2003 Malmgren et al. .......... 424/401

OTHER PUBLICATIONS

'Pressure' http://www.batesville.k12.in.us/physics/PhyNet/Mechanics/Newton2/Pressure.html pp. 1-3.*
Rohne, G. Extraction of Grape Seed Oil; Grasas y Aceites [Fats and Oils], vol. 22, Issue 5 (1971) pp. 393-400, pp. 1-14 of translated document.*
Wiemer et al. Small Scale Processing of Oilfruit and Oilseeds; Deutsche Gesellschaft fur Technische Zusammenarbeit, 1989, accessed from the internet of Jun. 29, 2005: URL <http://www5.gtz.de/gate/publications/G19Sme.pdf> pp. 1-92.*
Vitis Cold Pressed Grape Seed Oil Fat & Fatty Acid Profiles (2003) URL<www.vitis-vital.de>, 2 pages.

* cited by examiner

*Primary Examiner*—Patricia Leith
(74) *Attorney, Agent, or Firm*—John E. Drach

(57) ABSTRACT

The present application relates to a process for preparing cold-pressed grape seed oil, and to food, food supplements, food additives, animal food, animal food supplements, medicaments and cosmetics comprising the cold-pressed grape seed oil prepared by said process, and to the enrichment of various media with active substances, especially cyclic polyphenols, from the meal of the crushed seeds obtained in the process.

5 Claims, 2 Drawing Sheets

GRAPESEED, COLD-PRESSED GRAPE OIL, CRUSHED GRAPE AND GRAPE FLOUR

CROSS-REFERENCE TO RELATED APPLICATIONS

Figure 1:
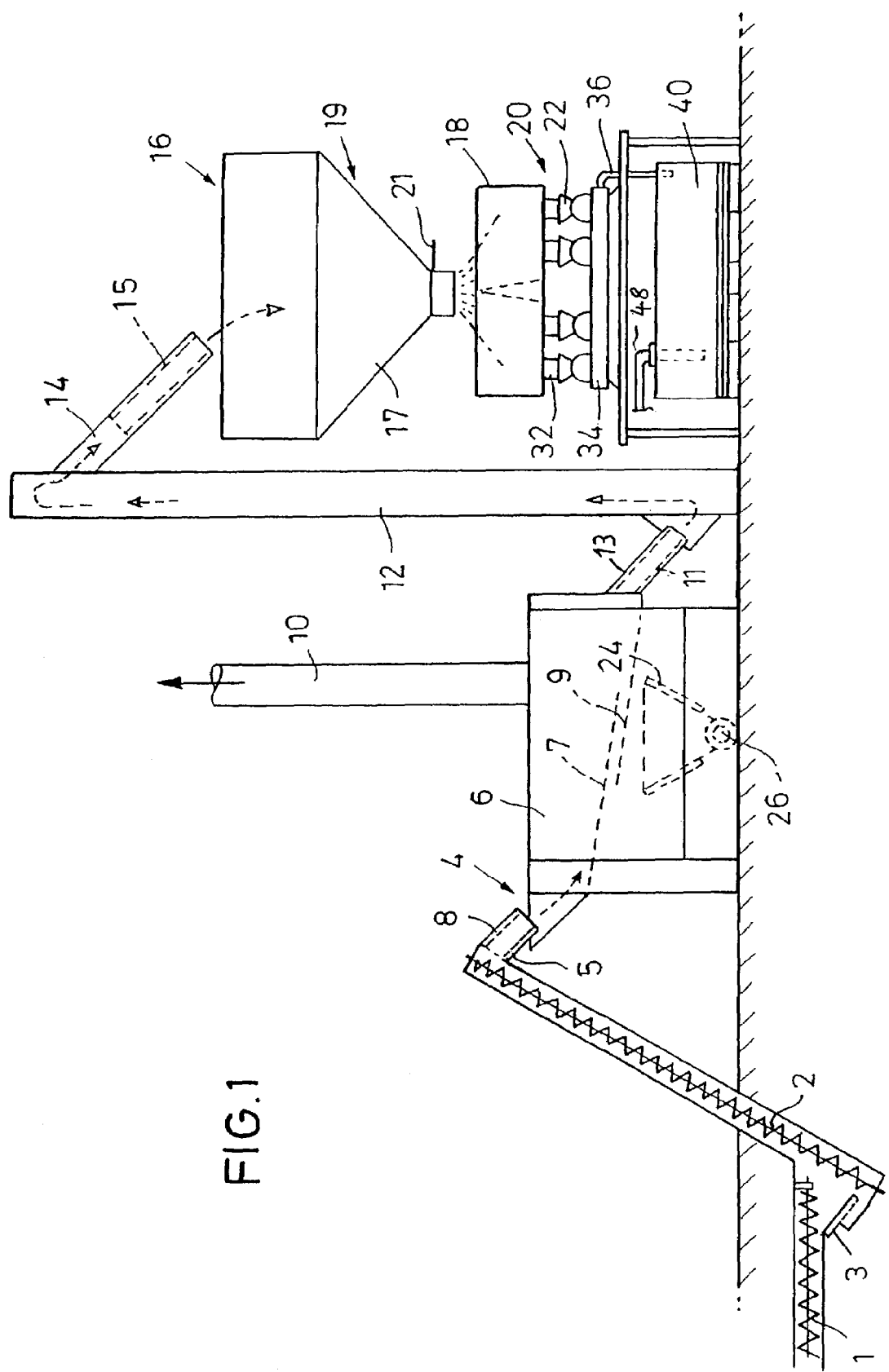

This application claims the benefit of the earlier filing date of International Patent Application No. PCT/EP00/07460, filed Aug. 2, 2000, under 35 U.S.C. § 120 and claims the benefit under 35 U.S.C. § 119 of German Patent Application Nos. 199 36 492.3 filed Aug. 5, 1999 and 100 15 006.3 filed Mar. 25, 2000.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Field of the Invention

The present application relates to a process for preparing cold-pressed grape seed oil, and to food, food supplements, food additives, fine food, animal food, animal food supplements, medicaments and cosmetics/skin care products comprising the cold-pressed grape seed oil prepared by said process, as well as to the enrichment of the above mentioned matters/agents, and also to the enrichment of wine and other beverages, cold-pressed grape seed oil and other oils with cyclic polyphenols and other active substances which can be extracted from the crushed seeds obtained in the process. The application also relates to the cold-pressed grape seed oil prepared by said process, the crushed seeds obtained in the process and mixtures thereof.

As early as in the Middle Ages, it was known that a high-value edible oil can be obtained from grape seeds by cold-pressing. This oil was further employed as an effective agent in cosmetics and as a remedy for treating small wounds, such as burns and skin lesions, and for the treatment of chapped skin (W. Heinen in "Das deutsche Weinmagazin", 14, July 1997). The traditional method of grape seed cold-pressing has completely fallen into oblivion and was replaced by modern extraction methods.

It is known that grape seeds have an extremely high and very specific content of cyclic polyphenols, such as procyanidines (epigallocatechin-3-gallates), e.g., catechin, its diastereomer epicatechin, the procyanidines B1, B2 and B3, and procyanidine C1, and various proanthocyanidines P1–P2. To all these natural compounds, commonly referred to as flavanols (containing a hydroxyphenyl residue), a high biological activity has been attributed for decades due to their excellent antioxidative potency.

As shown in more recent studies, cyclic polyphenols inhibit important receptors of the human cell membrane which are to be classified as 1-helix surface receptors and contribute to the formation and regulation of various growth hormones, but also insulin. This receptor type is formed by protein kinases which themselves serve a key function in intracellular signal transmission. They cause a change of biological activity by the phosphorylation of proteins. Main representatives are the tyrosine kinases which are actively involved in the over- and down-regulation of epithelial growth factor (EGF), platelet-derived growth factor (PDGF), fibroplast growth factor ($FGF_F$) and insulin receptor. By a "hyperfunction" or overexpression, these receptors can damage their cells and bring about a particular disease. The activation and inhibition of tyrosine kinases is related to diseases such as arteriosclerosis, arterial hypertension, growth and spreading of various tumors, skin diseases and insulin regulation.

Surprisingly, it has been found that the proportion of biologically active compounds, especially polyphenol compounds, in grape seed oils is extremely dependent on the nature of the pressing process, especially the pressing temperature and the degree of contamination of the starting seed material. Thus, the content of such polyphenols in grape seed oil obtained by hot extraction methods is significantly lower as compared to a traditional, "classical" cold-pressing process as described by W. Heinen in "Das deutsche Weinmgazin", 14 Jul. 1997.

It has now been found that the content of cyclic polyphenols of the cold-pressed grape seed oil can be improved by a careful purification of the material to be pressed from grape skins, stalks, stems etc. as well as by separating off metals (i.e., iron) and by controlling the pressing power and temperature. It has also been found that the remaining crushed seeds have extraordinarily high contents of cyclic polyphenols, and extracts of these materials from the meal of crushed seeds included in oil, wine and other liquids highly enrich the latter with the mentioned active substances.

Further, it has been found that the purification of the cold-pressed grape seed oil, if possible, should be effected by sedimentation because the active substances present in the cold-pressed grape seed oil can be obtained best in this way.

It could be shown that the content of polyphenol compounds in grape seed oil can be increased in a natural way by storing the grape seed oil, after the pressing process, on its crushed seeds meal without any auxiliaries, mechanical or chemical actions. Further, it has been found that both the thus prepared grape seed oil and the crushed seeds obtainable in the process as well as a mixture of both are an extremely effective food or food supplement for humans and animals, an effective medicament and active ingredient for cosmetics. There may be mentioned, in particular, the use for the treatment of skin diseases.

(2) Description of Related Art Including Information Disclosed Under 37 CFR 1.97 and 1.98. Not Applicable

BRIEF SUMMARY OF THE INVENTION

Thus, the present application relates to:

(1) a process for obtaining and processing highly purified grape seeds, comprising the steps of:
  (a) carefully drying the grape seeds; and
  (b) purifying the dried grape seeds, which includes the sieving and separating of metal parts using permanent magnets;

(2) a process for preparing cold-pressed grape seed oil (hereinafter also referred to as "grape seed oil"), comprising the drying and purifying of the grape seeds as described above under (1); and
  (c) pressing the purified grape seeds with a pressing power in the pressing head of from 50 to 100 kN to obtain cold-pressed grape seed oil and crushed seeds;

(3) a particular embodiment of the process described above under (2), further comprising the steps of:

(d) extracting components from the crushed seeds obtained by the process described under (2) by adding the cold-pressed grape seed oil obtained by a process as described under (2) or other edible oils to the crushed seeds;

(e) allowing the mixture obtained in step (d) to stand; and (f) separating the grape seed oil from the crushed seeds;

(4) food, food supplements, animal food, medicaments and cosmetics in all dosage forms, comprising:

(a) the cold-pressed grape seed oil as described under (1) to (3), especially that obtained by a process as described under (3);

(b) the crushed grape seeds obtained by a process as described under (1) and (2); or (c) a mixture of (a) and (b)

(5) a process for extracting components from the crushed seeds obtained by a process as described under (2), comprising the addition of a suitable extractant, such as oils, wine (white, rose or red wine) and other alcoholic and non-alcoholic beverages as well as other fluids, to the crushed seeds;

(6) food and food supplements containing the grape seeds obtained by the process as described under (1) and/or grape seed meal obtained from said grape seeds; and (7) the use of the mixture as defined in (4) for the treatment of skin diseases, especially psoriasis.

BRIEF DESCRIPTION OF THE SEVERAL VIEWS OF THE DRAWING(S)

Figure 2:
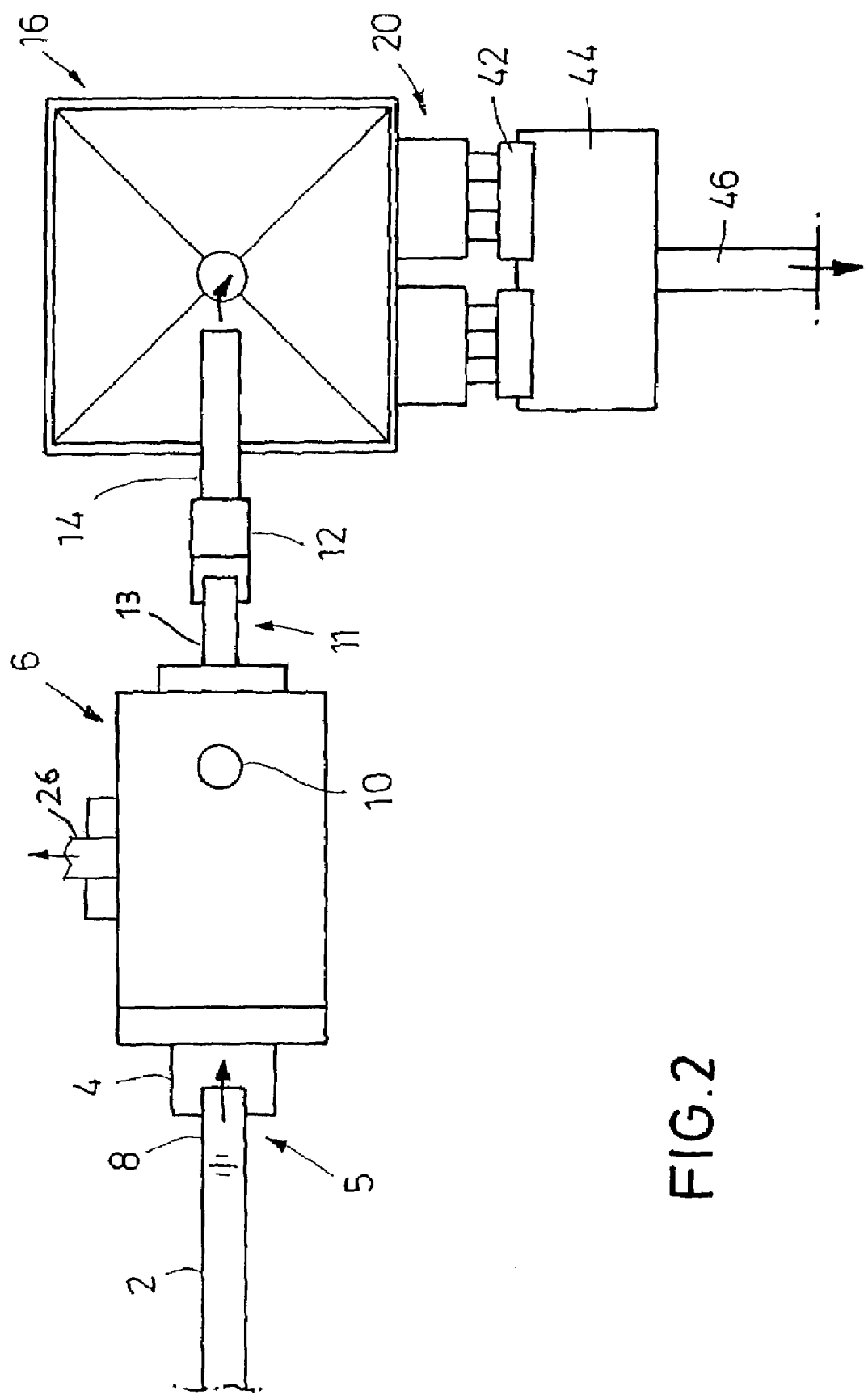

The present invention is further described in the following with reference to the drawings;

FIG. 1 shows a device according to the invention for the purification of grape seeds and for preparing cold-pressed grape seed oil and crushed seeds; and FIG. 2 is a top view of the device according to FIG. 1.

DETAILED DESCRIPTION OF THE INVENTION

In the process (1) according to the invention, drying is preferably effected in a current of air at an air temperature of from 50 to 70° C., preferably at from 55 to 60° C. (whereby the seed material is not significantly heated). By this drying, tissue material of the marc still adhering to the seeds is dried and separated from the seeds by the current of air. The chosen temperature range has proven advantageous for the content of polyphenol compounds in the final product (in the pressed oil as well as in the crushed seeds).

The sieving according to the present invention preferably comprises several sieving steps or the use of commercially available sieving machines (such as grain sieving machines) which have several sieving decks with different perforations. In addition, such a sieving device may be equipped with an exhausting system for removing the lightweight parts in the seed material (grape skins, dried tissue material) by exhausting. Several permanent magnets are employed in the purification line in order to remove any metal scraps from the seed material. The purification should achieve a purity of the seed material of greater than 97%, preferably greater than 99% (based on the weight of the seed material to be pressed), since contaminants cause decomposition of the active substances or reduce the yield of oil obtained.

As set forth above, the pressing of process (2) is effected at a pressing power in the pressing head (measured as axial load of the pressing screw) of from 50 to 100 kN, preferably at a pressing power of lower than 80 kN, but in such a way as to have a pressing temperature of the crushed seeds within the strainer basket of from 50 to 80° C., preferably from 50 to 60° C. (in screw presses, this pressing temperature is determined before the nozzle of the pressing head). The pressing temperature also depends on the degree of humidity and the respective seed material, in addition to the pressing power. However, to achieve as high as possible a content of polyphenols in the cold-pressed grape seed oil, it is required that the pressing temperature be as low as possible and by no means exceed 80° C. The temperature of the outflowing oil also depends on the pressing temperature; in the process according to the invention, it should be less than 50° C., preferably less than 40° C., when leaving the strainer basket. Then, the outflown oil will cool down in the sedimentation tank (see below) within a few seconds to temperatures of below 30° C.

Further, it was found that normal filtering reduces the content of polyphenol compounds in the pressed oil. According to the present invention, it is therefore preferred to free the cold-pressed oil from turbid matters in an additional sedimentation step. This sedimentation step is preferably performed in lightproof tanks (preferably of stainless steel). It is preferably performed in closed tanks to ensure substantial exclusion of oxygen.

In the process (3) of the present invention, steps (e) and (f) are performed at a temperature of less than 40° C. and more preferably less than 25° C. In a preferred embodiment of the process, the ratio of crushed seeds to grape seed oil in step (e) is within a range of from 5 to 40% by weight, preferably from 15 to 25% by weight; said allowing the mixture to stand is done in lightproof tanks; and/or the duration of the extraction process if from 10 to 120 days, preferably from 30 to 60 days. The separation in step (f) is performed as described in process (2).

The present invention further relates to food, food supplements, animal food and medicaments containing a mixture of cold-pressed grape seed oil and crushed seeds prepared by the process described above. The crushed seeds employed are derived from the process according to the invention (pressing residue or press cake). They may also be crushed seeds obtained by normal "crushing" of grape seeds. "Food/animal food" within the meaning of the present invention is food/animal food in the usual sense to which the mixture of grape seed oil and crushed seeds has been added. Food supplements are, for example, in the form of capsules or tablets for humans and animals and substantially consist of the mixture of grape seed oil and crushed seeds. The weight ratio of grape seed oil to crushed seeds in the food, food supplement, animal food and medicament of the present invention is preferably within a range of from 30:70 to 70:30, especially within a range of from 40:60 to 60:40.

The above described processes can be performed, preferably, by means of a device as shown in FIGS. 1 and 2 comprising a first conveying means (1,2) which supplies a seed material containing grape seeds to a sieving means (6) which separates the grape seeds from waste, metal parts and dust, a second conveying means (12) for conveying the grape seeds from the sieving means (6) to at least one oil pressing means (20) with a charging silo (16), wherein the grape seed oil is passed to an oil receiving vat (34), and the crushed seeds are passed to a crushed seeds receiving vat (44).

In the device, several magnetic separators (3, 5, 11, 15) are preferably arranged on the inlet side and/or outlet side on the sieving means (6) and/or the first and second conveying means 91, 2, 12). It is further preferred that a drying means is provided upstream from the sieving means (6).

Further, in the device, at least one sedimentation means (40) is provided downstream from the oil receiving vat (34). The above mentioned sieving means (6) preferably comprises an air separator means (10) which discharges dusty components of the seed material. Downstream from the oil pressing means (20), a pelletizing means (42) for crushed seeds may be provided.

The turbid matters separated off by sedimentation in the process according to the invention have a waxy paste-like consistency and exhibit a very high content of polyphenol compounds. In a particular embodiment, the food, food supplement, animal food and medicament according to the invention also still contains some proportion of these turbid matters in all known dosage forms. It is preferred that said medicament/food/food supplement/animal food respectively contain at least 10% by weight, more preferably at least 30% by weight, of cold-pressed grape seed oil, crushed seeds and turbid matters.

The food, beverages, fine food, food supplements, animal food and medicaments according to the invention may further contain commercially available minerals, carriers and additives as well as further foods and medicaments. It is preferred to add physiologically acceptable mineral salts, such as the lithium salts described in DE-A-41 27 469.5, such as lithium chloride and lithium carbonate.

Depending on its consistency (which depends on the oil content of the mixture and the consistency of the additives), the food supplement/medicament may optionally be provided with a coating acceptable for foods and medicaments to facilitate oral administration.

Another preferred form of application of the medicament according to the invention is cutaneous application, especially for the treatment of skin diseases. In this case, the medicament according to the invention is in the form of an ointment or plaster provided with the mixture of grape seed oil and crushed seeds according to the invention. Such a plaster is particularly suitable for the treatment of skin diseases, such as psoriasis, burns, skin irritations, such as sunburns and insect bites and stings, and small skin lesions, such as cuts and abrasions. Therefore, the present invention also relates to a process for the treatment of skin diseases, comprising the application of the above described mixture of grape seed oil and crushed seeds to the afflicted skin area. The above described mixture of grape seed oil and crushed seeds may also be a component of cosmetics, such as skin care agents and sunscreen agents.

Also, the extraction according to the invention of the active substances from the crushed seeds, especially the cyclic polyphenols, especially in oils, in wine and other beverages and fluids, can significantly increase the health-related activity of the mentioned agents by a sustained improvement of the active substance content within the scope of a health-oriented nutrition as well as in food supplementation, skin care, cosmetics and medicine.

The effect of the food or medicament according to the invention results from the fact that the different types of cyclic polyphenols, which are present in the grape seed oil and crushed seeds according to the invention at levels higher by a factor of 100 to 1,000 due to the mild treatment and enrichment, possess particularly important properties beneficial to health:

reduction of the blood alcohol level due to reduced absorption;

inhibition of the PDGF and NF factors in the generation of cardiovascular diseases in addition to further anti-oxidant properties;

inhibition of cellular growth via the important "early genes" (c-myc and c-fos proteins) in the nucleolus of the nuclei, which serve for the synthesis of DANN;

inhibition of cancer growth (stomach/esophagus/lung) (see GAO et al., 1994, J. Natl. Cancer Inst. 86: 855, 1994);

detoxifying enzyme activation and activation of programmed cell death (apoptosis) (Levitzki et al., Science 1995, 267: 1782);

inhibition of oncogenic gene expressions (proto-oncogen production) (Sanchinidis et al., Mol. Biol. of the Cell, 1999, 10: 1093);

inhibition by specific protein kinases of the TNF-α and IL-1 syntheses which is inhibited by the bacterial toxin, LPA (lipopolysaccharide), via the tyrosine kinases (Weinstein et al.; Natl. Acad. Sci. USA 1991, 88: 4148) and thereby could influence sepsis and rheumatoid arthritis; and long known anti-oxidative additional effect which is stronger than that of vitamin C and surpasses vitamin E and is generally accepted as a "free-radical scavenger".

Finally, it was found that the crushed seeds obtained in the process according to the invention is an excellent fertilizer for plants (both flowers and vegetables). The crushed seeds can be employed with or without additional fertilizers, such as mineral salts, and binders. Suitable mineral salts include, for example, the above-mentioned lithium salts.

The present invention is further illustrated by the following Example:

EXAMPLE

1. Pressing: Pressing is effected by means of a device as depicted in FIGS. 1 and 2.

1.1 Conveying to the sieving machine: The seed material is conveyed by first and second screw conveyors 1, 2 into the hopper 4 of the sieving machine 6. Between the first and second screw conveyors 1, 2 is provided a first permanent magnet means 3 for separating metal parts. At the end of the screw conveyor 2, the seed material falls through a tube 8 having a length of about 1 m into the hopper 4. A sensor is provided 50 cm above the discharge of this tube 8 into the hopper, which sensor switches off the conveying of both the first screw conveyor and the second screw conveyor 2 whenever the seed material has filled the receiving shaft 4 of the sieving machine 6 and then rises within the tube 8 to the level of the sensor.

On the tube 8 of the sieving machine (6) which leads to the hopper 4, there is a second permanent magnet device 5 which serves the function of separating off metal parts (pieces of wire, nails etc.) from the seed material.

1.2 Sieving machine: As the sieving machine 6, a commercially available grain sieving machine is used. It has two sieving means, wherein an upper sieving plate 7 has a perforation of 6 mm diameter, and a lower sieving plate 9 has a perforation of 3 mm. Further, the sieving machine 6 is equipped with an exhausting system 10 for lightweight parts in the seed material (grape skins), which also blows out the sieved-off dust overhead or laterally (very low dust recovery).

The upper and lower sieve plates 7, 9 are inclined towards an outlet tube 13 of the sieving machine 6. On the lower sieving plate 9, the grape seeds intended for pressing are accumulated and conveyed to the outlet tube 13, for example, by means of the agitating or vibrating means.

On the outlet tube 13 of the sieving machine 6, a further magnetic means 11 is provided. The outlet tube 13 passes the sieved grape seeds into an elevator 12.

The sieving machine 6 has three discharging shafts for the waste (sieved-off material):

a) coarse parts, which are vibrated off on the surface of the first sieving plate 7 (high sieve). These parts (pebbles, pieces of wood etc.) are disposed of as refuse. As known from experience, only an extremely small amount is obtained here which can be disposed into a cloth bag.

b) The waste from two further discharging shafts is collected in a receiving trough 24 using a small screw conveyor 26. The screw conveyor 26 is controlled by a sensor which is provided in the upper portion of the receiving trough about 20 cm below the upper edge and respectively initiates the screw conveyor 26 whenever the cone of discharged waste has reached this sensor.

c) The sieved-off material is passed by the screw onto another screw which conveys it onto a discharge heap.

d) In order to have sufficient ground clearance for this second screw (slope conveying), care is to be taken that the sieving machine 6 is mounted on a corresponding level. About additional 50 cm of ground clearance is necessary, which can be achieved by underlaying the support stands of the sieving machine 6 with glue-laminated timber.

1.3 Charging: The finely purified seed material is transferred into the charging silo 16 through the elevator 12 and a drop tube 14 subsequent to the elevator on whose end there is again a permanent magnet 15 (last magnet station for screening off any metallic residual parts).

The exit of the drop tube 14 is mounted so high that a cone of dropped material can form above the charging silo 16 in order to utilize the full storage capacity of this silo.

The charging silo 16 is positioned above oil-pressing means 20, so that the seeds can immediately reach the hoppers 22 of the oil presses by the natural slope in the distributor boxes 18. In practice, it has been found that the angle of the hopper walls 17 of the hopper 19 with the bottom of the charging silo 16 should be 55° to enable a smooth sliding of the seeds. When the angle is smaller, for example, 44°, it may occur that part of the seeds remains on the inclined hopper walls 17.

The seeds slide through the exit tube 30 of the charging silo 16, which can be closed by a slide gate 21, into the distributor trough 18, which protrudes into the hoppers 22 of the four oil-pressing means 20 with its four drop tubes 32 (plastic tubes of 100 mm diameter and about 150 mm length). The oil-pressing means 20 consist of screw presses.

Since the dropped seeds again form small cones in the hoppers 22, the flow of the seed material is automatically controlled, and a risk of overflow of the hoppers 22 does not exist even when the exit of the vertical drop tubes 32 of the distributor trough 18 is at the same level as the edge of the hoppers 22.

1.4 Pressing: There are used two Komet twin-screw presses of type DD85G with four modified pressing screws of type R8 and modified nozzles having a diameter of 15 mm.

The oil recovery and oil quality are determined by two factors:

a) Purity of the Material to be Pressed (Seeds)

The purer the seed material (i.e., free of grape skins and little stalks etc.), the better is the oil quality and the better is the recovery too, because the foreign matters result in a higher proportion of turbid matters, which absorb the pressed oil much like a sponge.

b) Pressing Power

The pressing power determines the oil quality (pressing temperature) and also the recovery yield.

The pressing power is affected by the pitch of the screw, by the revolutions per minute and by the nozzle cross-sectional area (the larger the nozzle aperture, the lower the pressing power).

In the optimum constellation of these factors acquired by practical experiments, the above mentioned modified pressing screws and nozzles have proven useful, and also a revolutions per minute of the screws, to be set through a friction clutch, which is around a value of 3.5 on the setting scale.

1.5 Pelletizing: The pressed seeds exist as a strand having a diameter which approximately corresponds to the nozzle aperture (15 mm) and would break into irregular strand segments of from 10 to 80 cm without further mechanical processing. In conveying the crushed seeds, larger hollow spaces would form with such strands, so that the total charge would have to be calculated lower. Also, the strands are less suitable for further processing, for example, in rough grinding mills.

For this reason, the strands are pelletized into segments of about 3 cm length. Thus, a pelletizing means 42 was constructed which chops the strands immediately after exiting from the nozzles of the oil-pressing means 20 using a blunt fly cutter with a highly reduced gear (low revolutions per minute) driven by a small electric motor. The length of the strand segments can be set by shifting the pelletizing means 42 on two rails mounted on the oil-pressing means 20, so that the fly cutter hits the pressed strand closer to or more remote from the end of the nozzles.

In further developing the above mentioned technology, a pelletizing machine was developed in which a screw conveyor rotates with variable revolutions per minute.

Between the tube wall and screw edge, the pressed strands are cut into pellets whose length can be predetermined by the revolutions per minute of the screw (controllable electric motor). The screw at the same time serves for conveying the pellets out onto another conveying means.

The pellets of the crushed seeds fall through a receiving trough 44 into a screw conveyor means 46 which conveys the crushed material onto a discharging heap or into a container/silo. The screw 46 is time-controlled: About every 40 minutes, the automatic system switches the screw 46 on for 30 seconds. This time is sufficient for completely conveying off the crushed seed material accumulated in the hopper 44. Due to this automatic timing, considerable energy expenses (current consumption) are saved as compared to a permanent operation of the screw 46, and the wear is kept low.

2. Oil 2.1 Receiving trough: Below the strainer baskets of the oil pressing means 20, there is a receiving trough 34 of stainless steel having a triangular cross-section and a slope towards the spout. Thus, it is ensured that the freshly pressed oil always drains off through a flexible plastic tube 36.

2.2 Sedimentation vat: The oil flows into a stainless steel sedimentation vat 40 having a rectangular cross-section and a capacity of 500 l. The sedimentation vat 40 is covered to avoid contamination by dust or foreign parts which could fall into the oil.

The sedimentation vat 40 serves the function to substantially withdraw turbid matters from the oil by natural sedimentation. Consequently, the outlet from the sedimentation vat 40 is to be provided in the form of a tube 48 which runs through a sleeve and can be fixed by fixing screws and thus be shifted to different levels, i.e., protrudes into the sedimentation vat 40 to different depths. Thus, by sucking off the uppermost oil layer, it can be avoided that a substantial proportion of turbid matter flows along with the oil into a container which is provided as a further stage of turbid matter sedimentation.

The oil conveying can be sufficiently accomplished by a small impeller pump with a 200 to 400 W motor (flexible tube material: plastic).

To obtain a filtered but clear oil which is suitable for marketing in this form, the oil must be pumped over at least once, preferably twice, after having been pumped over from the sedimentation vat 40 into the first container, so that filling is performed only from a third container. Since the cold-pressed grape seed oil, while being sensitive to neither heat nor cold and also being substantially resistant to oxidation, is highly light-sensitive, the oil containers should be permanently covered by a black plastic sheet.

2.3 Filtration: In the above described turbid matter sedimentation process, a residual turbid oil of about 20% of the total quantity remains. This oil having a high proportion of turbid matters must be filtered through cloth filters (chamber filter presses). Any filter press of this type can be employed.

To support the filtration effect, kieselguhr is stirred into the oil to be filtered (turbid oil mixture).

The oil thus produced is even clearer and more brilliant than the unfiltered one, but has a somewhat lower proportion of valuable substances and flavors.

The invention claimed is:

1. A process for preparing grape seed oil, said process comprising the steps of (a) drying grape seeds in a current of air at an air temperature of from 50 to 70° C.; (b) separating the dried grape seeds from impurities, said separation step comprising the sieving of the grape seeds from the impurities and magnetic separation of metal impurities from the grape seeds to obtain purified grape seeds; (c) pressing the purified grape seeds by means of a screw press wherein the axial load on the screw is from 50 to 100 kN and the temperature of the crushed grape seeds is −80° C. or less to obtain cold-pressed grape seed oil and crushed seeds; (d) separating the crushed seeds from the cold-pressed grape seed oil; (e) mixing the crushed grape seeds from step (d) with a cold-pressed grape seed oil extractant to extract cyclic polyphenols from the crushed grape seeds; wherein the ratio of crushed seeds to grape seed oil is within a range of from 15% to 25% by weight; (f) allowing the mixture obtained in step (e) to stand in a lightproof tank for 10 to 120 days to extract polyphenols front the crushed seeds; and (g) separating the grape seed oil obtained from step (f) from the crushed seeds.

2. The process according to claim 1, wherein the axial load is adjusted so that the pressing temperature of the crushed seeds is from 50 to 80° C.

3. The process according to claim 1, wherein the temperature of the oil after step (c) is less than 50° C.

4. The process according to claim 1, wherein steps (f) and (g) are performed at a temperature of less than 40° C.

5. The process according to claim 1 wherein step (f) is carried out for 30 to 60 days.

\* \* \* \* \*